(12) United States Patent
Justis et al.

(10) Patent No.: US 8,298,242 B2
(45) Date of Patent: Oct. 30, 2012

(54) SYSTEMS, DEVICES AND METHODS FOR BENDING AN ELONGATE MEMBER

(75) Inventors: Jeff R Justis, Germantown, TN (US); Dimitri K Protopsaltis, Memphis, TN (US); Hai H Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 180 days.

(21) Appl. No.: 12/770,921

(22) Filed: Apr. 30, 2010

(65) Prior Publication Data

US 2011/0270262 A1 Nov. 3, 2011

(51) Int. Cl.
*A61B 17/58* (2006.01)
*A61B 17/60* (2006.01)
*A61F 2/00* (2006.01)
*B21D 37/02* (2006.01)

(52) U.S. Cl. .......................... 606/101; 72/413

(58) Field of Classification Search .......... 606/250–265, 606/101; 72/19.8, 31.04, 364, 389, 390, 72/397, 413, 458; 700/165
See application file for complete search history.

(56) References Cited

U.S. PATENT DOCUMENTS

| | | |
|---|---|---|
| 3,866,458 A | 2/1975 | Wagner |
| 4,474,046 A | 10/1984 | Cook |
| 5,113,685 A | 5/1992 | Asher et al. |
| 5,161,404 A | 11/1992 | Hayes |
| 5,290,281 A | 3/1994 | Tschakaloff |
| 5,345,799 A * | 9/1994 | Miodushevski et al. ........ 72/19.8 |
| 5,389,099 A | 2/1995 | Hartmeister et al. |
| 5,490,409 A | 2/1996 | Weber |
| 5,548,985 A | 8/1996 | Yapp |
| 5,564,302 A | 10/1996 | Watrous |
| 5,591,165 A | 1/1997 | Jackson |
| 5,651,283 A | 7/1997 | Runciman |
| 5,658,286 A | 8/1997 | Sava |
| 5,819,580 A | 10/1998 | Gauthier |
| 5,938,662 A | 8/1999 | Rinner |
| 6,006,581 A | 12/1999 | Holmes |
| 6,035,691 A | 3/2000 | Lin et al. |
| 6,077,271 A | 6/2000 | Huebner |
| 6,128,944 A | 10/2000 | Haynes |
| 6,221,077 B1 | 4/2001 | Rinner et al. |
| 6,332,780 B1 | 12/2001 | Traxel et al. |
| 6,612,143 B1 | 9/2003 | Butscher et al. |
| 6,644,087 B1 * | 11/2003 | Ralph et al. ..................... 72/213 |
| 6,978,188 B1 | 12/2005 | Christensen |

(Continued)

FOREIGN PATENT DOCUMENTS

GB 2 267 757 12/1993

*Primary Examiner* — Sameh Boles

(57) ABSTRACT

Systems, devices and methods are provided for bending an elongate member used in a medical procedure. In one form, the device includes a bending mechanism having a plurality of engaging members are selectively positioned relative to a receiving area. In one embodiment, a first set of engaging members is positioned in a select arrangement, and a second set of the engaging members is movable relative to the select arrangement of the first set of engaging members to compressingly engage the elongate member to bend the elongate member to a desired shape/contour. The device also includes a heating element configured to apply heat to one or more portions of the elongate member to facilitate bending. In one form, the elongate member is formed of a heat deformable material, and heat is applied to soften one or more portions of the elongate member to provide added flexibility to facilitate bending.

29 Claims, 10 Drawing Sheets

U.S. PATENT DOCUMENTS

| | | |
|---|---|---|
| 7,115,129 B2 | 10/2006 | Heggeness |
| 2003/0055435 A1* | 3/2003 | Barrick .................. 606/102 |
| 2004/0144149 A1 | 7/2004 | Strippgen et al. |
| 2005/0203517 A1* | 9/2005 | Jahng et al. ............ 606/61 |
| 2005/0262911 A1 | 12/2005 | Dankowicz et al. |
| 2006/0150699 A1 | 7/2006 | Garner et al. |
| 2006/0235427 A1 | 10/2006 | Thomas et al. |
| 2006/0264934 A1 | 11/2006 | Fallin |
| 2006/0264973 A1 | 11/2006 | Abdelgany |
| 2007/0093824 A1 | 4/2007 | Hestad et al. |
| 2007/0227216 A1 | 10/2007 | Schalliol |
| 2007/0233079 A1 | 10/2007 | Fallin et al. |
| 2007/0233111 A1 | 10/2007 | Orbay et al. |
| 2008/0086127 A1 | 4/2008 | Patterson et al. |
| 2008/0125817 A1 | 5/2008 | Arnett et al. |

* cited by examiner

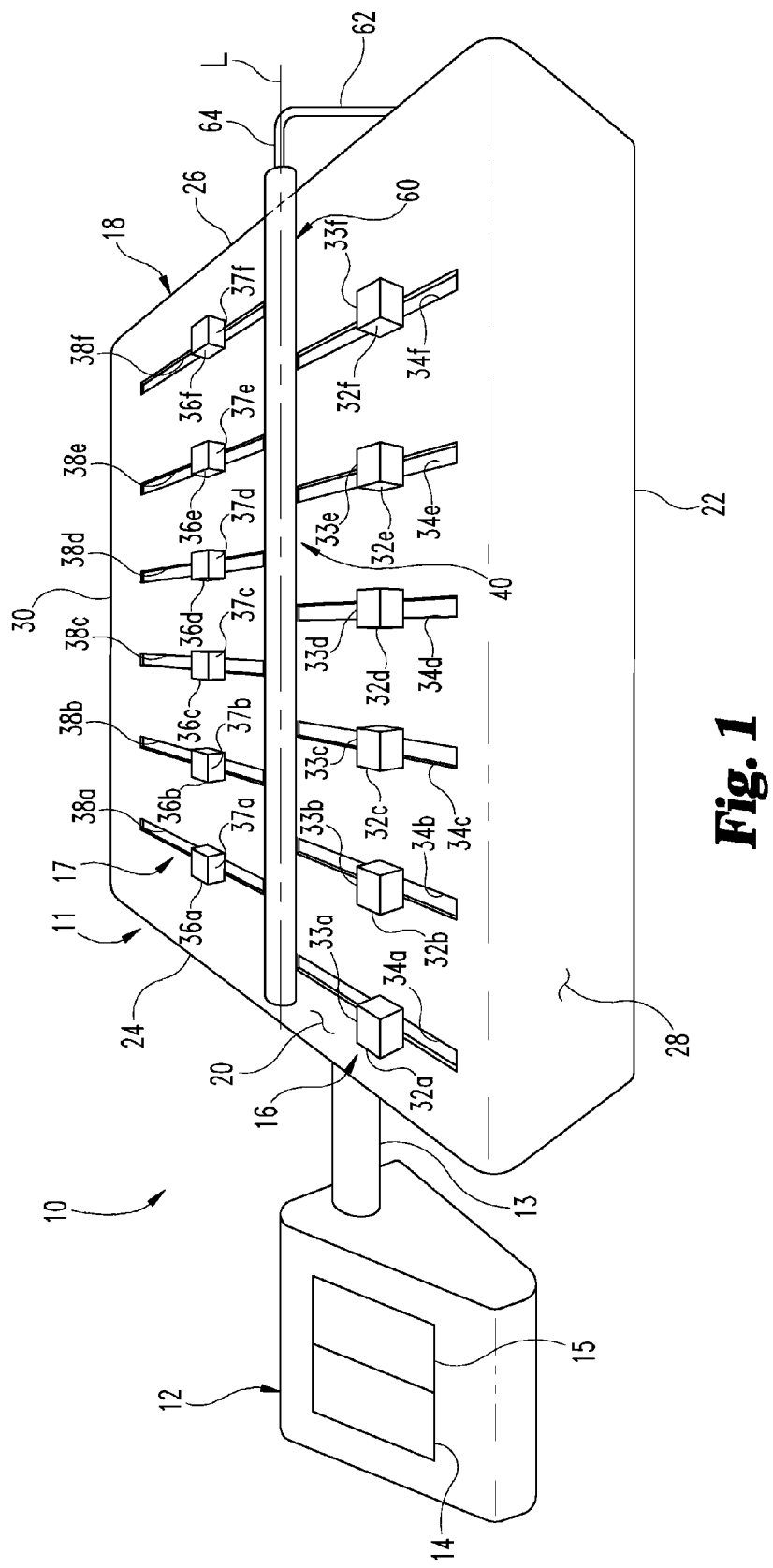

SYSTEMS, DEVICES AND METHODS FOR BENDING AN ELONGATE MEMBER

CROSS-REFERENCE TO RELATED APPLICATIONS

This application is related to a co-pending U.S. patent application entitled "SYSTEMS, DEVICES AND METHODS FOR MULTI-DIMENSIONAL BENDING OF AN ELONGATE MEMBER" filed on the same day as the subject application, the contents of which are hereby incorporated by reference in their entirety.

BACKGROUND

The present invention generally relates to systems, devices and methods for bending an elongate member used in association with a medical procedure. In one form, the medical procedure is a spinal stabilization procedure wherein an orthopedic construct is engaged along the spinal column, and the elongate member is a rod component anchored to the spinal column by a number of bone anchors.

The use of spinal constructs to stabilize and support a portion of the spinal column has become commonplace. In particular, spinal constructs frequently include several bone anchors that are anchored to various portions of the spinal column, and an elongate rod that extends between and is engaged with the bone anchors to provide stabilization and support to the spinal column. Typically, the elongate rod is initially provided in a substantially straight configuration, and is subsequently bent or contoured to facilitate engagement with each of the bone anchors and/or to provide a desired spinal curvature.

In the past, bending or contouring of elongate rods was accomplished by instruments or tools that relied solely on application of a mechanical bending force. However, prior techniques and instrumentation for bending elongate rods required application of excessive bending forces, and also risked fracturing or degradation of the elongate rod and/or degrading the material properties associated with the elongate rod. In this arena, the desire persists for improved rod bending/contouring capabilities. Thus, there is a need for additional contributions in this area of technology.

SUMMARY

One nonlimiting embodiment of the present invention is directed to a device for bending an elongate member used in association with a medical procedure. In one form of the present invention, the medical procedure is a spinal stabilization procedure, and the elongate member is a rod component anchored to the spinal column by a number of bone anchors. However, bending of other types of elongate members is also contemplated by the present invention. Additionally, the elongate member may be formed of a heat deformable material which softens or becomes less rigid as it is heated to provide increased flexibility to facilitate bending/contouring of the elongate member.

The device includes a bending mechanism having a plurality of engaging members structured and arranged for selective positioning relative to a receiving area of the device which is sized and configured to receive the elongate member. In one form, a first set of the engaging members is positioned in a select arrangement that corresponds to a desired shape or contour of the elongate member, and a second set of the engaging members is movable relative to the receiving area and the select arrangement of the first set of engaging members to compressingly engage the elongate member between the first and second sets of engaging member to bend the elongate member to a desired shape/contour. The device also includes a heating element configured to apply heat to one or more portions of the elongate member to facilitate bending/contouring of the elongate member. In one form, the elongate member is formed of a heat deformable material, and heat applied by the heating element softens the elongate member to provide added flexibility to facilitate bending. In a further form, the heating element is integral to the device and is arranged to apply heat to one or more portions of the elongate member positioned in the receiving area.

Another embodiment of the invention is directed to a unique system and method for bending a rod component used in association with a spinal implant construct. Other embodiments include unique methods, systems, devices, kits, assemblies, equipment, and/or apparatuses directed to the bending or contouring of an elongate rod component.

Further embodiments, forms, features, aspects, benefits, objects and advantages of the present invention will become apparent from the detailed description and figures provided herewith.

BRIEF DESCRIPTION OF THE FIGURES

FIG. 1 is a perspective view of one embodiment of a rod bending device.

DESCRIPTION OF THE ILLUSTRATED EMBODIMENTS

Figure 2A:
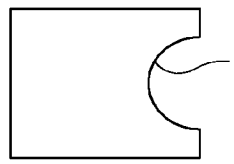
FIGS. 2a-2g are side views of various embodiments of rod engaging members for use in association with the rod bending device illustrated in FIG. 1.

For the purposes of promoting an understanding of the principles of the invention, reference will now be made to the embodiments illustrated in the drawings and specific language will be used to describe the same. It will nevertheless be understood that no limitation on the scope of the invention is intended. Any alterations and further modifications in the illustrated devices and described methods and further applications of the principles of the invention as disclosed herein are contemplated as would normally occur to one skilled in the art to which the invention relates.

Systems, devices and methods for bending or contouring an elongate member used in association with a medical procedure are provided. In one form, the medical procedure is a spinal stabilization procedure wherein a spinal construct is engaged along the spinal column. In a further form, the elongate member is a rod component anchored to the spinal column by a number of bone anchors to provide stabilization and support to the spinal column. However, other types of elongate members are also contemplated for use in association with the present invention, including plate components or other suitable types of elongate support components. In one embodiment, the bone anchors are initially anchored to portions of the spinal column, followed by engagement of the rod component to the bone anchors. The rod component may require bending or contouring to allow for interconnection with the bone anchors and/or to provide a desired spinal curvature. The spinal construct may be used in association with, but is not limited to, treatment of degenerative spondylolisthesis, fracture, dislocation, scoliosis, kyphosis, or spinal tumors.

Figure 8:
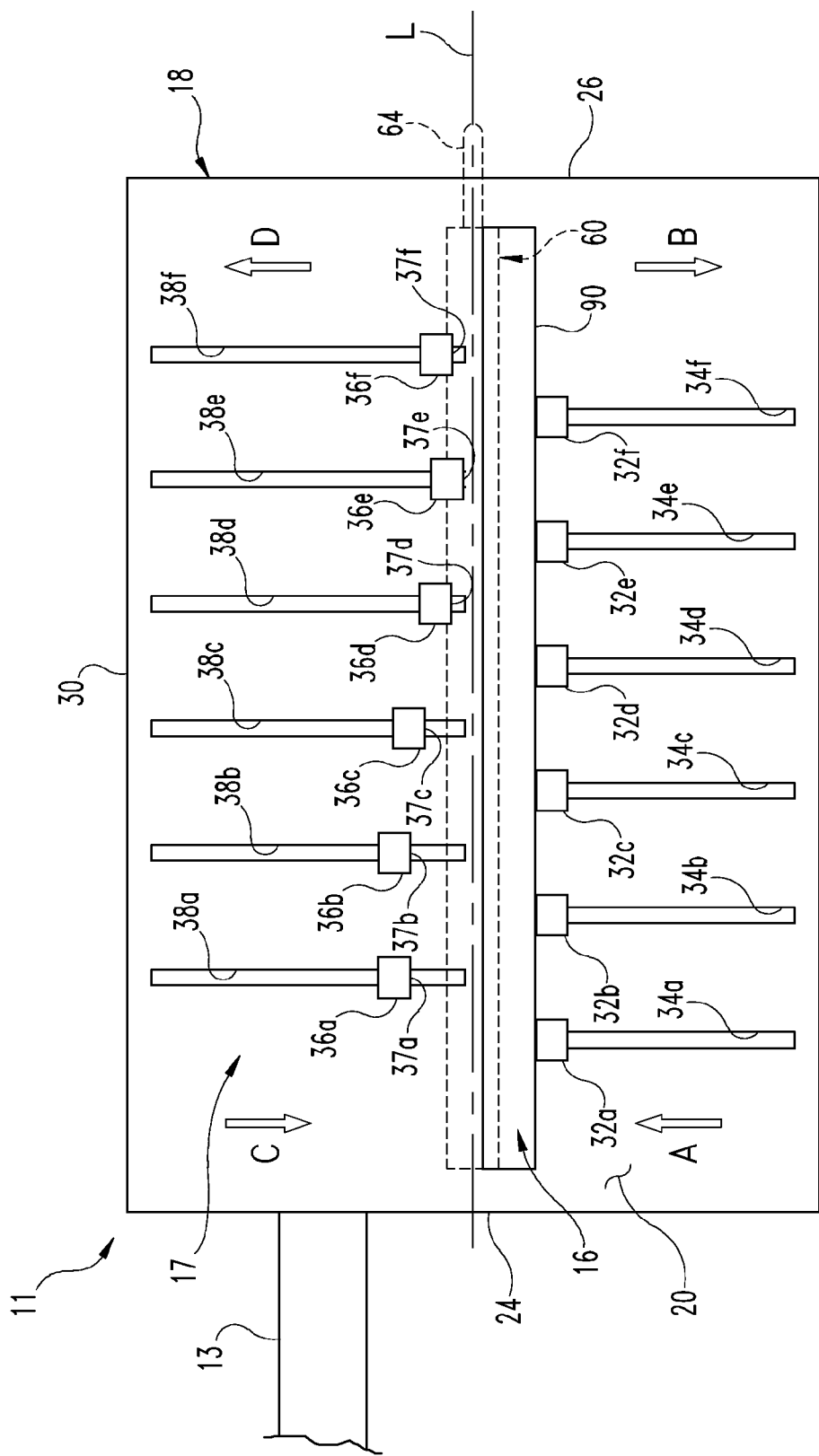
FIG. 8 is a top plan view of the rod bending device illustrated in FIG. 1, as engaged with an elongate rod member in a first operational position.
Figure 9:
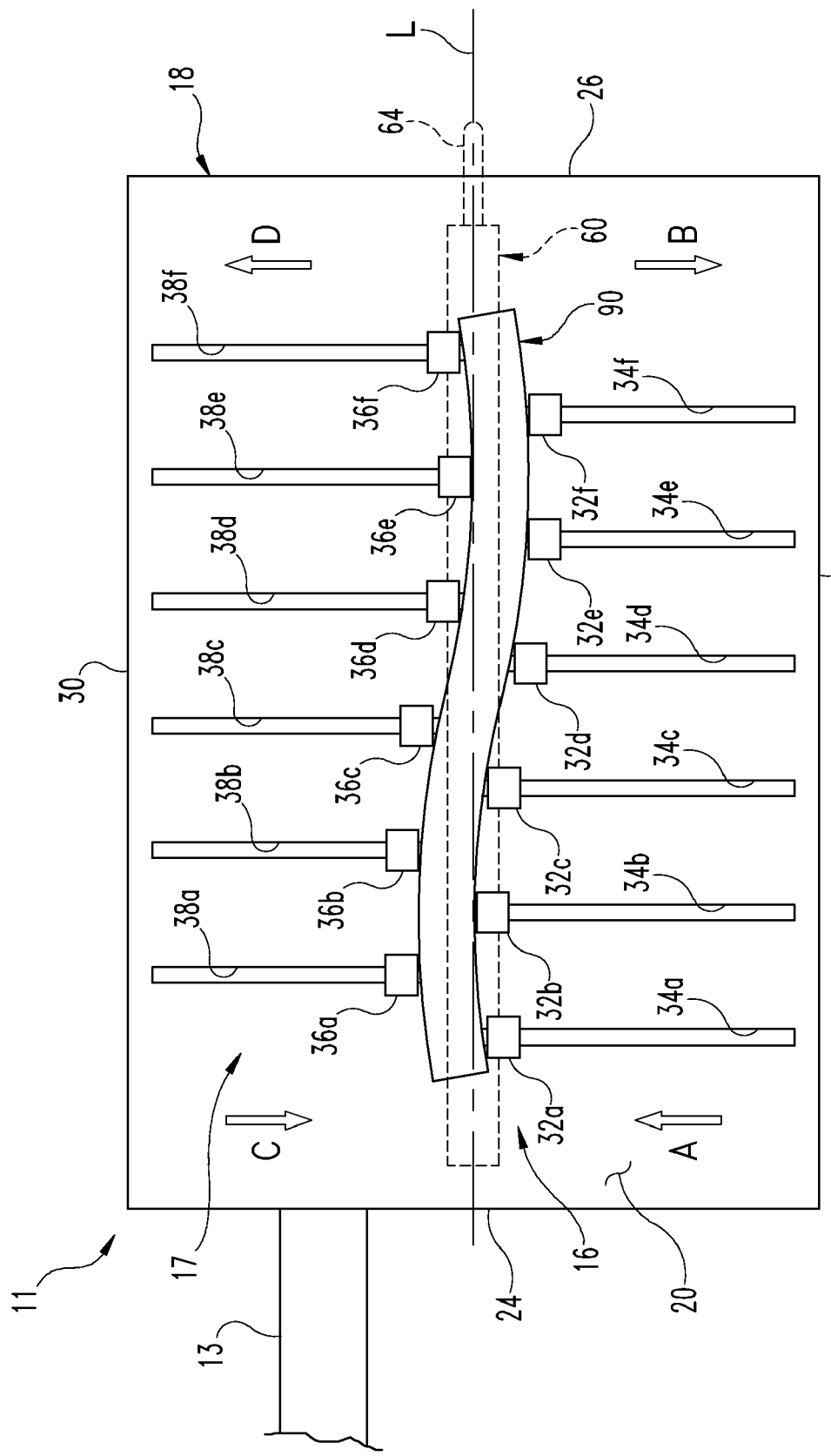
FIG. 9 is a top plan view of the rod bending device illustrated in FIG. 1, as engaged with an elongate rod member in a second operational position.

Referring to FIG. 1, illustrated therein is a device 10 according to one form of the present invention for bending or contouring an elongate rod member 90 (FIGS. 8 and 9). As indicated above, other types of elongate members are also contemplated for use in association with the present invention, including plate components or other suitable types of elongate support components. The device 10 includes a bending mechanism 11 operably coupled with a user interface 12 via a pathway 13. Further details regarding the user interface 12 will be set forth below. However, it should be appreciated that in other embodiments, the device 10 need not be provided with the user interface 12. The bending mechanism 11 is structured to bend or contour the elongate rod member 90 at one or more axial locations along the length of the rod 90. The bending mechanism 11 includes a housing 18 including a top wall 20, a bottom wall 22, a first lateral side wall 24, a second lateral side wall 26, a front wall 28 and a back wall 30. However, it should be appreciated that the illustrated configuration of the housing 18 is exemplary, and that housings having other sizes, shapes and configurations are also contemplated. The bending mechanism 11 generally includes a first rod engaging portion 16 positioned generally opposite from a second rod engaging portion 17. A rod receiving area 40 is generally positioned intermediate the first and the second rod engaging portions 16, 17 and arranged generally along a longitudinal axis L extending between the lateral side walls 24, 26. In the illustrated embodiment, the bending mechanism 11 has a generally open configuration and is structured and arranged to facilitate relatively unobstructed viewing of the rod 90 as the rod 90 is bent or contoured. However, alternative configurations contemplate one or more covers or housings that partially or entirely enclose the bending mechanism 11.

The first rod engaging portion 16 includes a first set of movable and selectively positionable rod engaging members 32a-f, with the rod engaging members 32a-f having rod engaging faces 33a-f, respectively, that generally face the rod receiving area 40. The second rod engaging portion 17 includes a second set of movable and selectively positionable rod engaging members 36a-f, with the rod engaging members 36a-f having rod engaging faces 37a-f, respectively, that generally face the rod receiving area 40. In one embodiment, the rod engaging members 32a-f are positioned intermediate adjacent pairs of the rod engaging members 36a-f. In other words, the rod engaging members 32a-f are axially offset from (i.e., not aligned laterally opposite) the rod engaging members 36a-f. In one specific embodiment, the rod engaging members 32a-f are generally centered between adjacent pairs of the rod engaging members 36a-f. However, it should be understood that other positions and arrangements of the rod engaging members 32a-f relative to the rod engaging members 36a-f are also contemplated. It should also be appreciated that the first and second rod engaging portions 16, 17 may be provided with a different number of the rod engaging members 32a-f, 36a-f than what is specifically illustrated in FIG. 1.

In the illustrated embodiment of the bending mechanism 10, the rod engaging members 32a-f, 36a-f each have a generally rectangular-shaped outer profile. However, in other embodiments, the rod engaging members 32a-f, 36a-f may be provided with outer profiles defining other shapes and configurations, including polygonal, oval, elliptical or circular shapes and configurations, or any other suitable shape or configuration that would occur to one of ordinary skill in the art. Furthermore, in the illustrated embodiment, the rod engaging faces 33a-f, 37a-f each have a generally flat or planar configuration. However, it should be understood that the rod engaging faces 33a-f, 37a-f may be provided with non-planar geometric configurations or contours to facilitate smooth bending of the rod member 90 while maintaining constant and secure engagement with the rod engaging members 32a-f, 36a-f. For example, the rod engaging faces 33a-f, 37a-f may be provided with a curved configuration including concave and/or convex shapes, an angled configuration including triangular or polygonal shapes, a curvilinear configuration including curved portions and linear portions, or any other suitable geometric configuration. It is also contemplated that each of the faces 33a-f, 37a-f may be provided with a channel or groove configured to receive a portion of the rod member 90 such that the rod engaging members 32a-f, 36a-f at least partially surround an outer periphery of the rod member 90. Additionally, in one embodiment, the faces 33a-f, 37a-f of the rod engaging members 32a-f, 36a-f are each provided with smooth surface finish to avoid scratching, gouging or otherwise damaging the outer surface of the rod member 90. However, in other embodiments, the faces 33a-f, 37a-f of the rod engaging members 32a-f, 36a-f may be somewhat roughened and/or provided with one or more gripping elements to facilitate secure engagement with the rod member 90.

Referring to FIGS. 2a-2g, shown therein are embodiments of rod engaging members having various geometric configurations or contours suitable for use in association with the present invention. However, it should be understood that the embodiments illustrated in FIGS. 2a-2g are exemplary, and that other embodiments of the rod engaging members are also contemplated for use in association with the present invention.

Figure 2B:
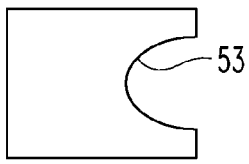
Figure 2C:
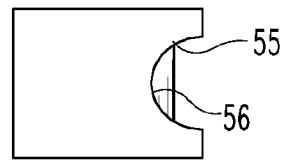
Figure 2D:
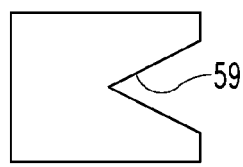

FIG. 2a illustrates an embodiment of a rod engaging member 50 including a rod engaging face 51 having a semi-circular or C-shape, FIG. 2b illustrates an embodiment of a rod engaging member 52 including a rod engaging face 53 having an elliptical or U-shape, and FIG. 2c illustrates an embodiment of a rod engaging member 54 including a rod engaging face 55 having a semi-circular or C-shape with a convexly-curved bottom surface 56 having a saddle-like configuration to allow pivotal movement of the rod member 90 about the convexly-curved bottom surface 56. It should be understood that any of the embodiments of the rod engaging members may be provided with a convexly-curved bottom surface having a saddle-like configuration to facilitate pivotal movement of the rod member 90 relative to the rod engaging face. FIG. 2d illustrates an embodiment of a rod engaging member 58 including a rod engaging face 59 having a V-shape, and FIG. 2e illustrates an embodiment of a rod engaging member 60 including a rod engaging face 61 having a curvilinear shape including a circular bottom portion 62 and a pair of angled flat/planar portions 63a, 63b tapering outwardly and away from the circular bottom portion 62.

Figure 2E:
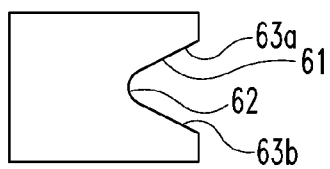
Figure 2F:
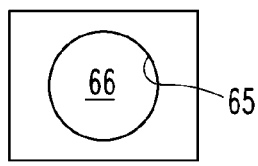
Figure 2G:
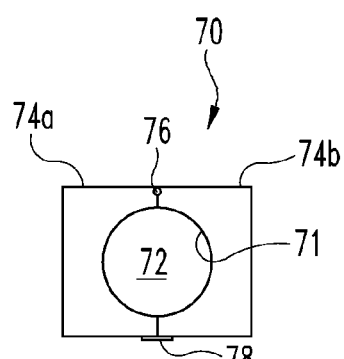

Additionally, FIG. 2f illustrates an embodiment of a rod engaging member 64 including a rod engaging face 65 defining an enclosed circular-shaped opening 66 formed by a unitary, single-piece rod engaging element, and FIG. 2e illustrates an embodiment of a rod engaging member 70 including a rod engaging face 71 defining an enclosed circular-shaped opening 72 formed by a pair of rod engaging elements 74a, 74b that are pivotally coupled to one another via a pivot or hinge element 76. The rod engaging elements 74a, 74b may be maintained in a closed or captured position via a latch or lock element 78. As should be appreciated, the rod member 90 is engaged with the rod engaging member 64 by axially loading the rod member 90 into the circular-shaped opening 66, whereas the rod member 90 may be engaged with the rod engaging member 70 by pivoting the rod engaging elements 74a, 74b to an open position and laterally loading the rod member 90 into half of the circular-shaped opening 72 defined by one of the rod engaging elements 74a, 74b, followed by pivoting the other rod engaging elements 74a, 74b about the pivot element 76 to a closed position to capture the rod member 90 within the circular-shaped opening 72, and maintaining the rod engaging elements 74a, 74b in the closed or captured position via the latch element 78.

In the illustrated embodiment of the bending mechanism 10, the top wall 20 of the housing 18 includes a plurality of elongated apertures 34a-f, 38a-f formed therein. As illustrated in FIG. 1, the elongated apertures 34a-f are axially offset from (i.e., not aligned laterally opposite) the elongated apertures 38a-f. The rod engaging members 32a-f, 36a-f are movably mounted within respective ones of the elongated apertures 34a-f, 38a-f. In this configuration, the rod engaging members 34a-f, 38a-f are movable or slidable along the length of the elongated apertures 34a-f, 38a-f in directions toward and away from the receiving area 40 such that the rod engaging members 34a-f, 38a-f may be selectively positioned at select locations along the elongated apertures 34a-f, 38a-f.

Figure 3:
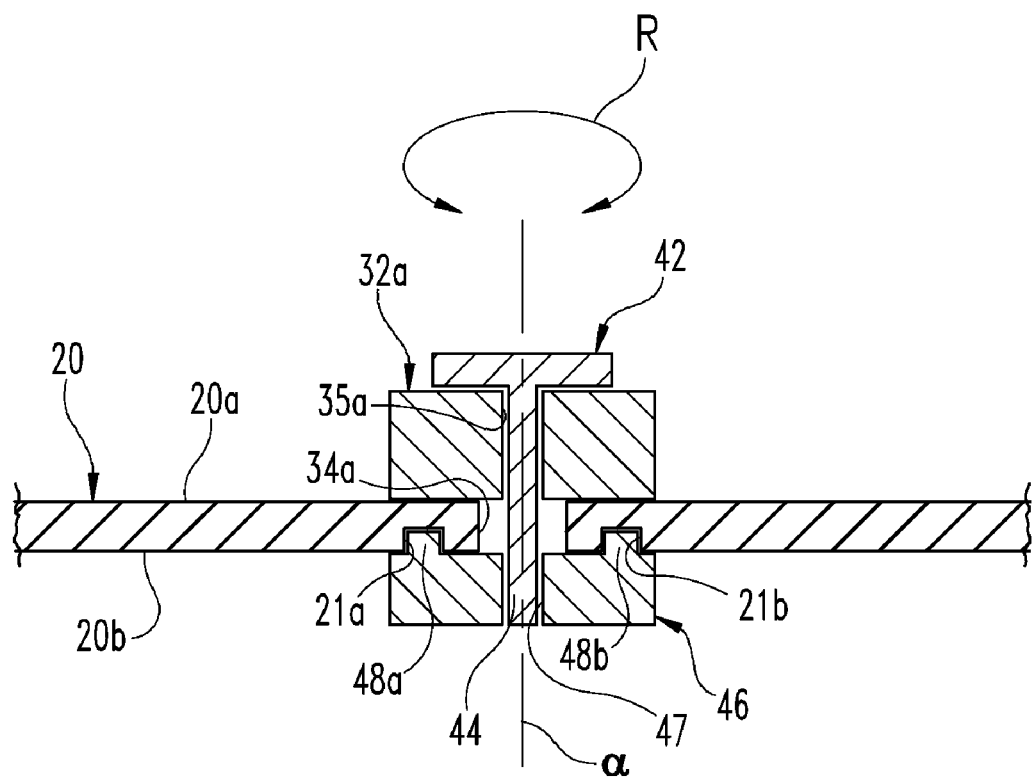
FIG. 3 is an enlarged cross-sectional view of one embodiment of a rod engaging member for use in association with the rod bending device illustrated in FIG. 1.

Referring to FIG. 3, shown therein are further details regarding the rod engaging member 32a according to one embodiment of the present invention. It should be appreciated that the details regarding the rod engaging member 32a are equally applicable to the remaining rod engaging members 32b-f and 36a-f. In the illustrated embodiment, the rod engaging member 32a is operatively connected to a coupling member 46 by a connector 42. The rod engaging member 32a includes an aperture 35a through which a portion of the connector 42 extends. In one embodiment, the connector 42 includes an externally threaded stem 44 that is threadingly engaged within an internally threaded aperture 47 in the coupling member 46. However, it should be appreciated that other suitable connection arrangements between the rod engaging member 32a and the coupling member 46 are also contemplated as falling within the scope of the present invention.

In the illustrated embodiment, the coupling member 46 includes a pair of oppositely positioned extensions or protrusions 48a, 48b which extend toward the rod engaging member 32a and which are sized for sliding receipt within slots or grooves 21a and 21b defined by the upper wall 20 of the housing 18. The slots 21a, 21b are formed in a lower surface 20b of the upper wall 20, but preferably do not extend entirely through the upper wall 20 to the upper surface 20a. The slots 21a, 21b are positioned on opposite sides of the elongated aperture 34a and extend along the length of the elongated aperture 34a. As should be appreciated, the slots 21a, 21b serve to guide the coupling member 46 and the rod engaging member 32a along the length of the elongated aperture 34a. Although not specifically illustrated in FIG. 3, it should be appreciated that one or both of the slots 21a, 21b and the extensions 48a, 48b can be configured and arranged to prevent the extensions 48a, 48b from becoming disengaged from the slots 21a, 21b. For example, in one exemplary embodiment, the extensions 48a, 48b and the slots 21a, 21b may be provided with a dovetail or T-shaped configuration to prevent disengagement of the extensions 48a, 48b from the slots 21a, 21b, while still allowing the extensions 48a, 48b to freely slide along the length of the slots 21a, 21b. Although a specific arrangement for coupling the rod engaging member to the housing 18 has been illustrated and described herein, it should be understood that other arrangements are also contemplated as would occur to one of skill in the art.

As also illustrated in FIG. 3, the rod engaging member 32a is mounted to the housing 18 in a manner which allows the rod engaging member 32a to rotate about an axis of rotation a in the direction of arrows R. Engagement of the extensions 48a, 48b within the slots 21a, 21b preferably restricts or inhibits rotation of the coupling member 46 relative to the housing 18. However, the rod engaging member 32a is rotatably coupled to the coupling member 46 via the connector 42 so as to allow selective rotation of the rod engaging member 32a relative to the coupling member 46 (and the housing 18) about the axis of rotation a in the direction of arrows R. Once the rod engaging member 32a is positioned at a select location along the length of the elongated aperture 34a and at a select orientation relative to the axis of rotation a, the threaded stem 44 of the connector 42 is threaded into the threaded aperture 47 in the coupling member 46. Threading of the connector 42 into the threaded aperture 47 in turn draws the rod engaging member 32a and the coupling member 46 toward one another and clampingly engages the top wall 20 of the housing 18 therebetween, thereby fixing the position and orientation of the rod engaging member 32a relative to the receiving area 40 of the bending mechanism 11. As should be appreciated, unthreading or loosening of the connector 42 from the threaded aperture 47 unclamps the rod engaging member 32a and the coupling member 46 from the top wall 20 of the housing 18, thereby allowing further adjustment to the position and orientation of the rod engaging member 32a. As should also be appreciated, the connector 42 need not necessarily be tightened to clamp the rod engaging member 32a against the coupling member 46. Instead, the rod engaging member 32a may be allowed to freely rotate relative to the coupling member 46 during the rod bending process to allow the orientation of the rod engaging member 32a to vary relative to the coupling member 46.

While not specifically illustrated in the drawing figures, it should be appreciated that one or both of the connector 42 and the coupling member 46 may be configured to prevent complete disengagement of the connector 42 from the coupling member 46, which in turn prevents disengagement of the rod engaging member 32a from the coupling member 46. For example, in one embodiment, a cross pin may be positioned through an aperture in the threaded stem 44 at a location below the coupling member 46. If the threaded stem 44 becomes disengaged from the threaded aperture 47, the cross pin contacts a lower surface of the coupling member 46 to prevent the coupling member 46 from disengaging the connector 42 and the rod engaging member 32a. In another embodiment, the connector 42 may be provided with an enlarged lower flanged portion which contacts a lower surface of the coupling member 46 to prevent disengagement of the coupling member 46 from the rod engaging member 32a. In a further embodiment, the coupling member 46 may be configured as a lock nut structured to prevent disengagement of the connector 42 from the coupling member 46.

It should also be appreciated that various arrangements may be utilized to displace the rod engaging members 32a-f, 36a-f to select positions and/or orientations relative to one another and relative to the rod receiving area 40 of the bending mechanism 11. For example, in one embodiment, each of the rod engaging members 32a-f, 36a-f may be individually coupled to and movable by a respective rack and pinion mounting structure. Each rack and pinion structure includes a rack portion coupled to one of the engaging members 32a-f, 36a-f, and a respective pinion portion coupled to the housing 18. However, a reverse configuration is also contemplated wherein the rack portion is coupled to the housing 18 and the pinion portion is coupled to one of the engaging members 32a-f, 36a-f. Each pinion portion includes a pinion gear that engages teeth formed along the rack portion. Rotation of the pinion gear displaces the corresponding rod engaging member to position the rod engaging member at a select location relative to the rod receiving area 40 of the bending mechanism 11. The pinion gear may be driven by various types of drives including, for example, an electric or pneumatic motor. In other embodiments, linear drives including, for example, pneumatic cylinders or electric screws, may be utilized to selectively position the rod engaging members 32a-f, 36a-f relative to one another and relative to the rod receiving area 40. Still further embodiments for facilitating selective positioning of the rod engaging members 32a-f, 36a-f include ball-detent mechanisms and releasably interlocking cams or tabs, just to name a few other possibilities.

Selective positioning of the rod engaging members 32a-f, 36a-f allows the rod engaging members 32a-f of the first rod engaging portion 16 to be selectively positioned and arranged relative to the rod engaging members 36a-f of the second rod engaging portion 17 located on the opposite side of the rod receiving area 40 and the longitudinal axis L. As will be described in further detail below, selective positioning of the rod engaging members 32a-f, 36a-f relative to one another allows the elongate rod member 90 to be bent to a desired shape/contour. When the elongate rod member 90 is positioned at the rod receiving area 40 between the first and second rod engaging portions 16, 17, relative movement of the rod engaging members 32a-f toward the rod engaging members 36a-f compressively engages the rod engaging members 32a-f and 36a-f against the elongate rod member 90 to thereby bend the elongate rod member 90 to a desired contour or curvature along one or more portions of the rod length. As should be appreciated, the contour or curvature of the elongate rod member 90 is dictated or governed by the particular position and orientation of the individual rod engaging members 32a-f and 36a-f relative to one another and relative to the elongate rod member 90.

As shown in FIG. 1, the device 10 further includes a heating mechanism or element 60 positioned adjacent the bending mechanism 11. In the illustrated embodiment, the heating element 60 is positioned external to the housing 18 between the first and second rod engaging portions 16, 17 and is generally aligned with the longitudinal axis L and the rod receiving area 40. As illustrated in FIG. 1, a support member 62 extends from the lateral side wall 26 of the housing 18 to an offset portion 64 which is coupled to the heating element 60 to mount the heating element 60 in a select position and orientation relative to the rod receiving area 40. In the illustrated embodiment of the device 10, the heating element 60 is generally centered over the rod receiving area 40. In this arrangement, the heating element 60 provides a relatively uniform application of heat to the elongate rod member 90 when the elongate rod member 90 is positioned at the rod receiving area 40. However, in other non-illustrated embodiments, the support member 62 may be adjustable to facilitate adjustable positioning of the heating element 60 toward or away from the elongate rod member 90 and/or in direct contact with the elongate rod member 90. In one alternative embodiment, the support member 62 may be formed of a multi-directional flexible material to allow adjustable positioning of the heating element 60 in a plurality of positions and orientations, including a position that is in direct contact with the elongate rod member 90. Additionally, in the illustrated embodiment, the heating element 60 is configured to apply heat to substantially the entire length of the elongate rod member 90. However, in other embodiments, the heating element 60 may be configured to apply heat to select axial portions of the elongate rod member 90 such as, for example, to the particular portions of the elongate rod member 90 to be bent by the bending mechanism 11. Furthermore, although the heating element 60 is illustrated as a single element having a linear configuration, it should be understood that the heating element 60 may be comprised of multiple segments/elements and/or may be provided with a curved configuration, a curvilinear configuration, an angled configuration, or any other suitable configuration.

Figure 4:
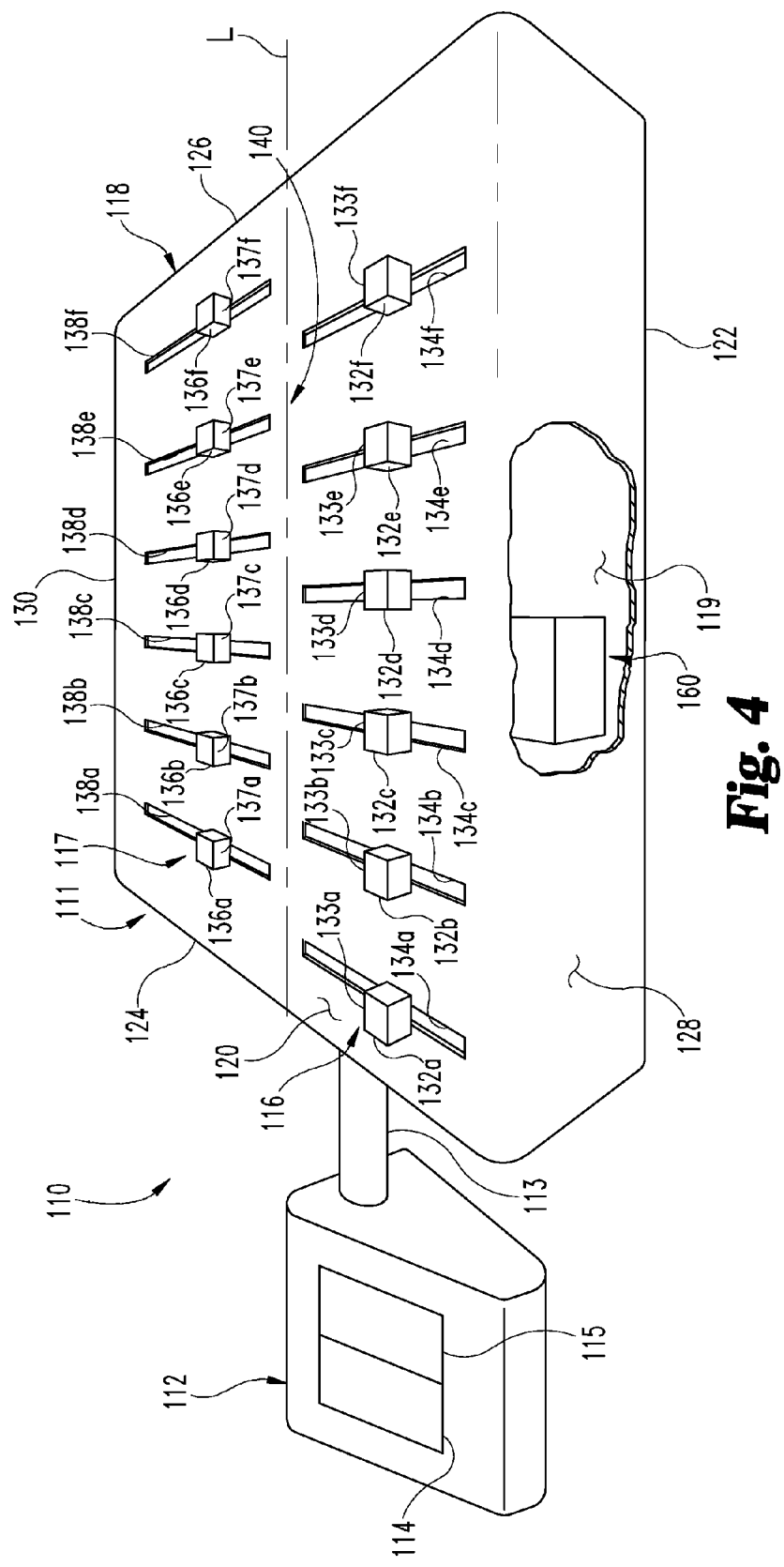
FIG. 4 is a perspective, partial cut-away view of another embodiment of a rod bending device.

Although a particular configuration of the heating element 60 is illustrated in FIG. 1, it should be understood that other configurations are also contemplated. For example, FIG. 4 illustrates an embodiment of a device 110, with like numerals referring to like features previously described above with regard to device 10. The device 110 includes an alternatively arranged heating element 160. Unlike the device 10 where the heating element 60 is positioned external to the housing 18, the device 110 includes a housing 118 including an internal chamber 119 within which the heating element 160 is internally positioned. In this arrangement, the heating element 160 provides heat to the rod receiving area 140 and to the elongate rod member 90 (when positioned at the rod receiving area 140) via the elongated apertures 134a-f, 138a-f. In another embodiment, the top wall 120 of the housing 118 may be provided with one or more apertures in addition to the elongated apertures 134a-f, 138a-f to facilitate the application of heat from the heating element 160 to the rod receiving area 140 and the elongate rod member 90. It is also contemplated that the top wall 120 may be formed of a mesh material to facilitate the application of heat from the heating element 160 to the rod receiving area 140 and the elongate rod member 90. In still other embodiments, the top wall 120 may be formed of a thermally-conductive material so as to readily transfer heat from the heating element 160 to the rod receiving area 140 and to the elongate rod member 90. As discussed above with regard to the heating element 60 of the device 10, the heating element 160 of the device 110 may be configured to apply heat to substantially the entire length of the elongate rod member 90 or to select axial portions of the elongate rod member 90.

The heating elements 60, 160 are generally structured to apply heat to one or more portions of the rod member 90, or the entire length of the rod member 90, when positioned adjacent the rod receiving area 40, 140. The heating element 60, 160 may take any form or configuration suitable to apply heat to the elongate rod member 90. For example, the heating element 60, 160 may be configured to provide heat via convection heating, conduction heating, infrared heating, or any other type of heating known to those of skill in the art. Additionally, the heating element 60, 160 may utilize power from an internal or external power source to provide heat in a variety of manners including, for example, via a coil resistance heater, a metal oxide resistance heater, or a PTC (Positive Temperature Coefficient) heater, just to name a few possibilities. In one particular embodiment, the heating element 60, 160 comprises an infrared heating element. In other embodiments, the heating element 60, 160 comprises a band heater and/or a cartridge heater. In still other embodiments, the heating element 60, 160 directs hot air toward the rod member 90. It is also contemplated that the heating element 60, 160 may be positioned in direct contact with the elongate rod member 90 to heat the rod member 90 via conductive heat transfer. Other suitable arrangements or configurations of the heating elements 60, 160 are contemplated in addition to or in lieu of those specifically described above. Furthermore, in addition to applying heat to the rod member 90, the heating elements 60, 160 may also be configured to control or regulate the temperature of the rod member 90 via various cooling or refrigeration systems including, for example, convection cooling by way of air, water or other convective media and/or conductive cooling systems, further details of which will be set forth below.

Figure 5:
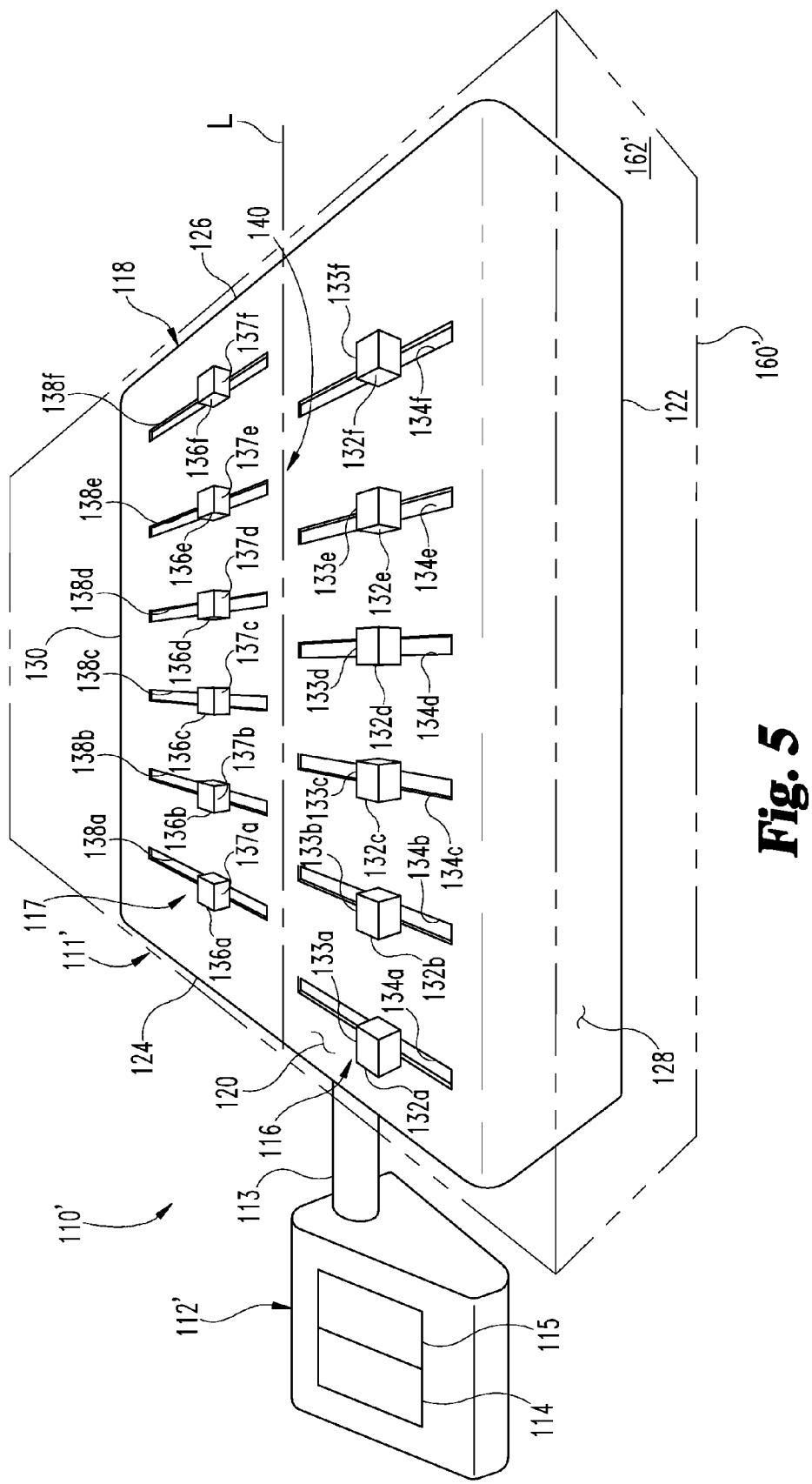
FIG. 5 is a perspective view of another embodiment of a rod bending device.

Referring to FIG. 5, shown therein an embodiment of a device 110', with like numerals referring to like features previously described above with regard to the devices 10 and 110. Unlike the devices 10, 110 which include heating elements 60, 160 positioned externally or internally relative to the bending mechanism 11, 111, respectively, the device 110' includes an environmental chamber or heating/cooling vestibule 160' defining an enclosed interior region 162' within which the bending mechanism 111' is positioned, and with the user interface 112' positioned external to the enclosed interior region 162'. As should be appreciated, the environmental chamber 160' controls or regulates the temperature of the rod member 90 as well as the bending mechanism 111'. In one embodiment, the environmental chamber 160' controls or regulates temperature via convection heating using air, water or other heating media. It should be appreciated that the environmental chamber 160' may control or regulate temperature via various types of heating systems including, for example, coil resistance heating, metal oxide resistance heating, PTC (Positive Temperature Coefficient) heating, radiant heating, infrared heating, and/or conduction heating by way of direct contact with a heating element, just to name a few possibilities. Furthermore, in addition to controlling temperature via heating, the environmental chamber 160' may control or regulate temperature via cooling or refrigeration systems including, for example, convection cooling using air, water or other cooling media and/or conduction cooling by way of direct contact with a cooling element. Additionally, as should be appreciated, the environmental chamber 160' may be configured to control the temperature of the entire length of the rod member 90 or the temperature of select axial portions of the rod member 90.

The heat applied to the elongate rod member 90 by the heating elements 60, 160 or the environmental chamber 160' facilitates bending of the elongate rod member 90 via relative movement of the rod engaging members 32a-f, 36a-f to select positions that define a particular pathway or bend axis between the rod engaging members 32a-f, 36a-f that corresponds to a particular rod curvature or contour. In one embodiment of the invention, the elongate rod member 90 is formed from one or more heat deformable materials. In a more specific embodiment, the heat deformable material(s) comprises one or more thermoplastic polymers. Examples of thermoplastic polymers include, for example, high molecular weight organic polymers. More particular examples of thermoplastic polymers include, without limitation, polycarbonate, polyketone, polyester, polyethylene, polyetheretherketone (PEEK), polyimide, polylactic acid, polypropylene, polystyrene, polysulfone, polyvinyl chloride, polyamide, poly(tetrafluoroethene), polyphthalamide, polybutylene and mixtures thereof, just to name a few possibilities. In one particular embodiment, the elongate rod member 90 is formed from a polyetheretherketone (PEEK) material. It is also contemplated that the elongate rod member 90 may be formed of other materials which, when heated, facilitate bending of the elongate rod member 90 to a desired configuration having a particular curvature or contour. For example, the elongate rod member 90 may be formed from one or metals or metal alloys including, for example, titanium, titanium alloys, chrome-cobalt (CrCo), stainless steel, or shape-memory materials such as Nitinol.

In other embodiments, the elongate rod member 90 may be formed as a composite material including, for example, a carbon or metal reinforced thermoplastic polymer or PEEK material, an inner core material surrounded by a thermoplastic polymer or PEEK outer sleeve material, or a thermoplastic polymer or PEEK inner core material surrounded by an outer sleeve material different from the inner core material. In one embodiment, the inner core material or the outer sleeve material may be formed of a metallic material such as, for example, titanium or stainless steel. However, the use of non-metallic inner core materials or non-metallic outer sleeve materials are also contemplated. In embodiments utilizing composite rod members 90 that include a metallic inner core or a metallic outer sleeve, heating of the thermoplastic polymer or PEEK material may be accomplished by passing current through the metallic material. As should be appreciated, passing current through a resistive metallic material will cause the metallic material to heat up, which may in turn be used to heat the thermoplastic polymer or PEEK material to facilitate bending of the rod member. Additionally, in embodiments utilizing composite rod members 90 that include a metallic inner core or a metallic outer sleeve, heating of the thermoplastic polymer or PEEK material may be accomplished by heating the metallic material via conduction heating (i.e., by placing a heat source in direct contact with the metallic material). As should be appreciated, the heated metallic material in turn applies heat to the thermoplastic polymer or PEEK material to facilitate bending of the rod member. Furthermore, in embodiments utilizing composite rod members 90 that include an inner core, the inner core may be provided with an axial passage extending therethrough. In this embodiment, controlling the temperature of the thermoplastic polymer or PEEK material may be accomplished by passing a convective heating/cooling media through the axial passage to promote convective heat transfer between the media and the inner core member. As should be appreciated, the inner core member may in turn be used to control the temperature of the thermoplastic polymer or PEEK material to facilitate bending of the rod member.

As indicated above, the device 10 may be provided with a user interface 12. The user interface 12 may include a visual display 14 configured to provide information related to the bending mechanism 11, the heating element 60, 160, the environmental chamber 160' and/or the elongate rod member 90 to a surgeon or other medical professionals. The user interface 12 may also be configured to provide other types of perceptible indications including audio or touch indications configured to provide information relative to the components of the device 10 to a surgeon or other medical professionals. For example, the information provided by the user interface 12 may include an indication as to the temperature of the heat applied to the rod 90 by the heating element 60, 160 or the environmental chamber 160', and/or the temperature of one or more portions of the rod member 90. The user interface 12 may also provide a perceptible indication to the surgeon or other medical professionals once the rod member 90 has reached an appropriate bending temperature, which in turn indicates when the bending mechanism 11 may be actuated to bend the elongate rod member 90. The visual display 14 can be of a Cathode Ray Tube (CRT) type, Liquid Crystal Display (LCD) type, plasma type, Organic Light Emitting Diode (OLED) type, a printer, or other types of visual displays that would occur to those skilled in the art. The user interface 12 may also include a user input 15 wherein, in one non-limiting example, a user may enter one or more commands to control the heat applied to the rod 90 by the heating element 60, 160 and/or the bending operation performed by the bending mechanism 11. The user input 15 may also include a keyboard, mouse or other pointing device, a voice recognition input subsystem, and/or different operator input apparatus that would occur to those skilled in the art. In one or more alternative embodiments, it is also contemplated that the device 10 may be provided without a user interface 12.

As indicated above, the rod engaging members 32a-f or 36a-f are selectively positionable relative to one another and relative to the rod receiving area 40 to an arrangement defining a particular pathway or bend axis between the rod engaging faces 33a-f, 37a-f of the rod engaging members 32a-f, 36a-f that corresponds to a desired curvature or contour of the elongate rod member 90. When the elongate rod member 90 is positioned within the rod receiving area 40 between the first and second engaging portions 16, 17, relative movement of the rod engaging members 32a-f or 36a-f toward one another (i.e., toward the longitudinal axis L) brings the rod engaging members 32a-f and 36a-f into compressive contact with the elongate rod member 90, which in turn bends the elongate rod member 90 to a desired contour or curvature corresponding to the pathway or bend axis defined between the faces 33a-f, 37a-f of the rod engaging members 32a-f, 36a-f.

Figure 6:
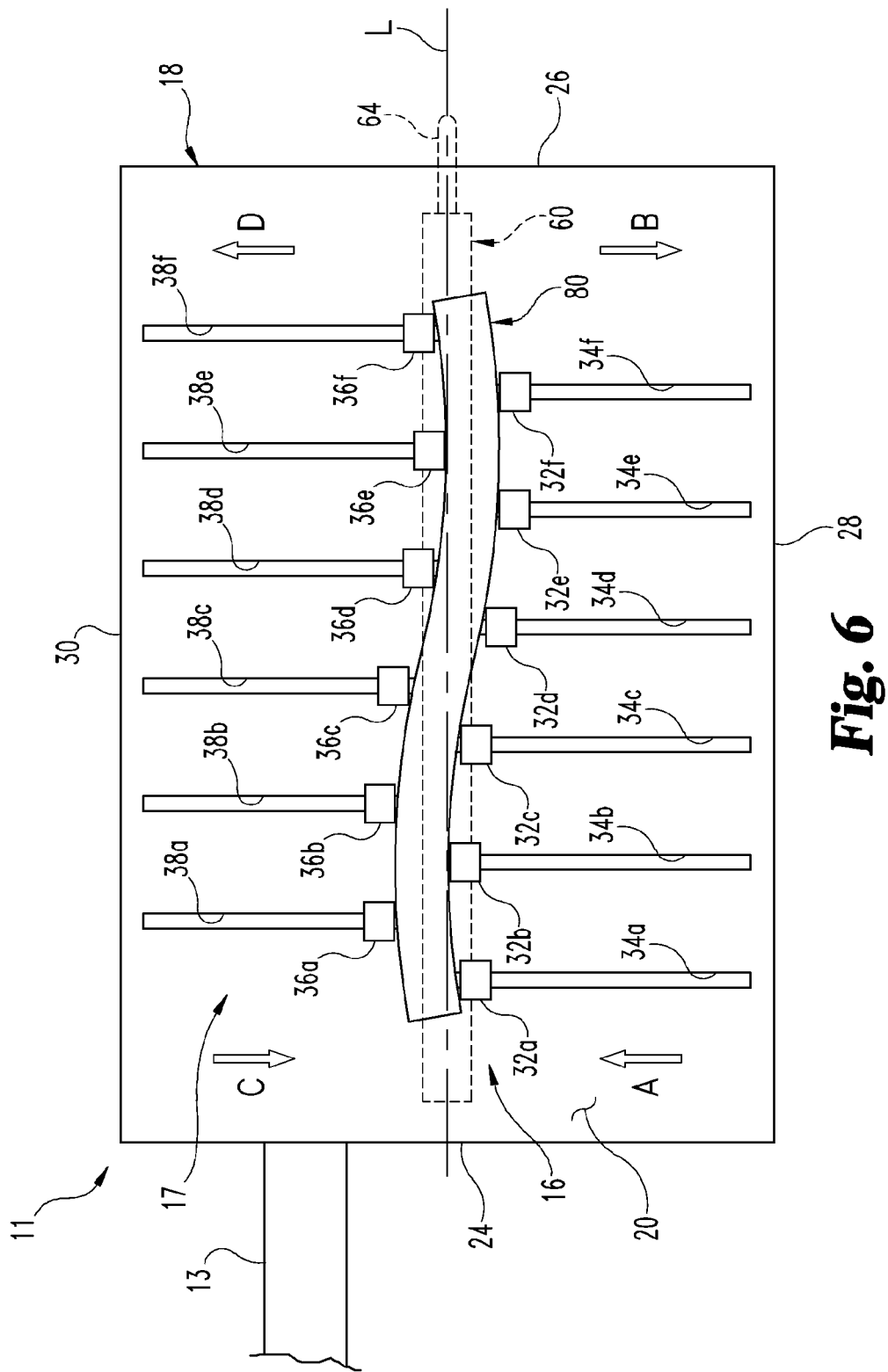
FIG. 6 is a top plan view of the rod bending device illustrated in FIG. 1, as engaged with a template rod member.

Further functional and operational aspects of the device 10 are set forth in the following description related to FIGS. 6-9. For the sake of clarity, the heating element 60 and the offset portion 64 of the support 62 have been illustrated in phantom in FIGS. 6-9. However, it should be understood that the heating element 60 may be replaced or supplemented by the heating element 160 and/or the environmental chamber 160'. In FIG. 6, a template rod 80 having a select contoured profile is positioned at the rod receiving area 40. In one embodiment, the template rod 80 generally has the same length, size and cross-sectional shape as the elongate rod member 90. The contoured profile of the template rod 80 corresponds to the desired shape/contour of the elongate rod member 90 subsequent to bending by the device 10. In one embodiment, the template rod 80 is formed of a material amenable to manual bending or bending via conventional bending tools or instruments. In a specific embodiment, the template rod 80 is formed of a non-rigid, flexible material. In a more specific embodiment, the template rod 80 is formed of aluminum or an aluminum alloy. The template rod 80 may initially be provided in a straight configuration and then bent, either manually or with conventional bending tools or instruments, to a shape/contour that corresponds to the particular position of bone anchors attached to the spinal column to which the elongate rod member 90 will eventually be engaged. While the illustrated template rod 80 has been bent to include multiple bends, it should be appreciated that in other embodiments, the template rod 80 may include a single bend or one or more bends in addition to or in lieu of those specifically illustrated in FIG. 6.

Figure 7:
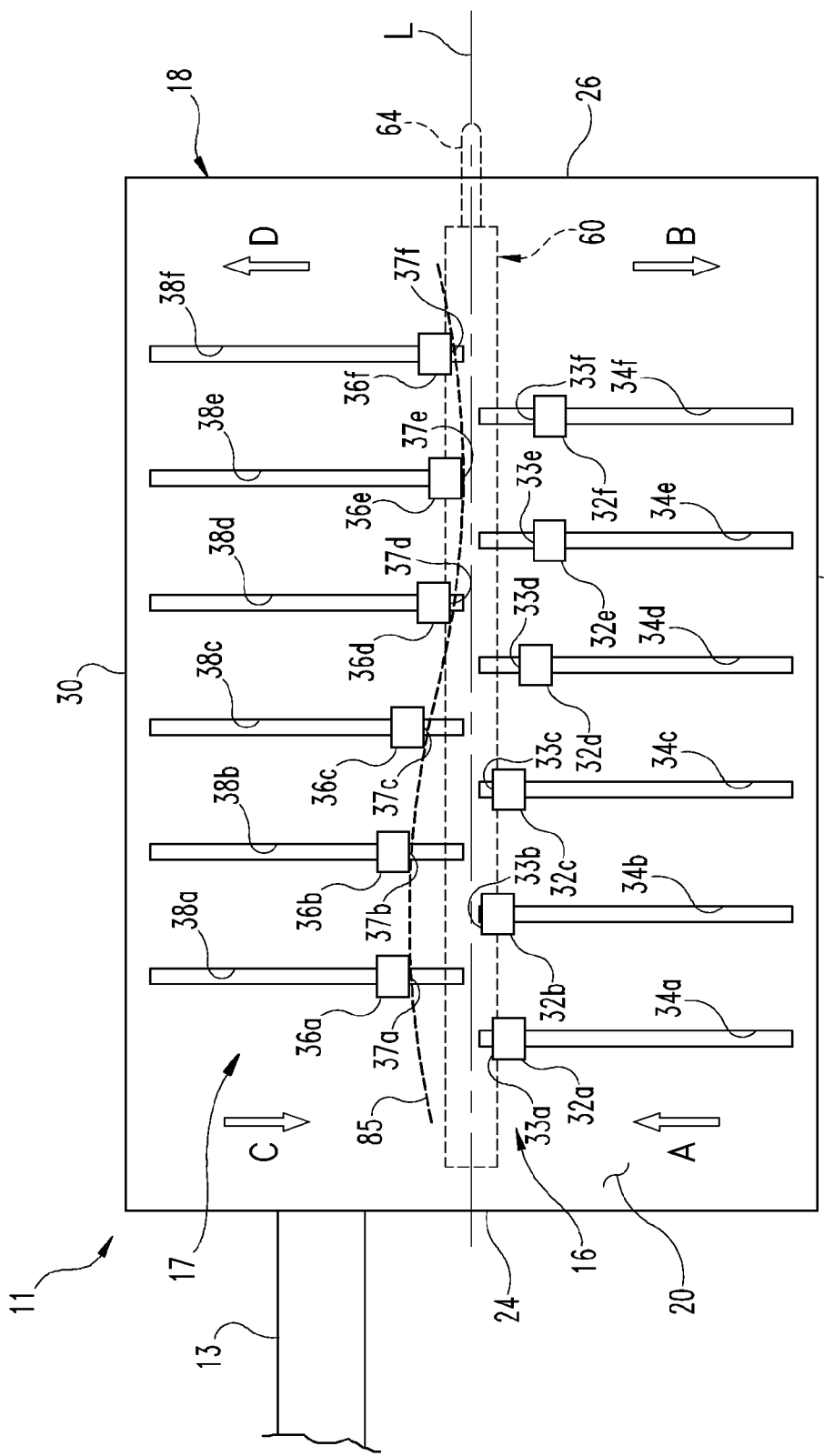
FIG. 7 is a top plan view of the rod bending device illustrated in FIG. 6 following removal of the template rod member.

As further illustrated in FIG. 6, the rod engaging members 32a-f and 36a-f are displaced toward one another and toward the longitudinal axis L, as indicated by directional arrows A and C, respectively, until the rod engaging faces 33a-f, 37a-f come into contact with the template rod 80 positioned within the rod receiving area 40. In this manner, the rod engaging members 32a-f, 36a-f of each of the first and second rod engaging portions 16, 17 are positioned relative to one another in an arrangement that corresponds to the contoured shape of the template rod 80. At this point, the relative position/arrangement of the rod engaging members 32a-f, 36a-f may be manually or electronically recorded. As illustrated in FIG. 7, the rod engaging members 32a-f may be moved away from the rod engaging members 36a-f in the direction indicated by arrow B. As the rod engaging members 32a-f are moved in the direction of arrow B, the rod engaging members 32a-f disengage the template rod 80, and the template rod 80 may be removed from the rod receiving area 40. The rod engaging members 36a-f may remain fixed at their respective positions relative to the rod receiving area 40, and thereby retain their position/arrangement that corresponds to the contoured shape of the template rod 80, as indicated by the dashed line 85.

Referring to FIG. 8, the elongate rod member 90 is positioned in the bending mechanism 11 at the rod receiving area 40 between the first and second rod engaging portions 16, 17. More particularly, the elongate rod member 90 is positioned against the rod engaging faces 33a-f of the rod engaging members 32a-f. Once the rod 90 is suitably positioned in the bending mechanism 11, the heating element 60 is actuated and heat is applied to one or more portions of the rod 90. In one exemplary embodiment where the rod 90 is at least partially formed of a thermoplastic polymer such as PEEK, the heating element 60 heats the rod 90 until the thermoplastic polymer approaches or exceeds the glass transition temperature ($T_g$). As would be appreciated by those skilled in the art, as the thermoplastic polymer approaches or exceeds the glass transition temperature $T_g$, the material becomes less rigid and more flexible. As a corollary, once the rod 90 is heated in this manner, a user may initiate bending of the rod 90 via the bending mechanism 11. In one embodiment, a visual or audible indication may be provided to the user via the user interface 12 which indicates that the rod 90 has achieved a sufficient degree of flexibility, and that the user may begin bending/contouring of the rod 90 via actuation of the bending mechanism 11. After a sufficient amount of heat is applied to the rod 90 and the rod 90 has achieved a sufficient degree of flexibility, the user may initiate movement of the rod engaging members 32a-f toward the rod engaging members 36a-f, as indicated by arrow A, which in turn correspondingly compresses the rod 90 into engagement with at least some of the engaging members 36a-f of the second engaging portion 17 to initiate bending of the rod 90 relative to the arrangement of the rod engaging members 36a-f.

Relative movement of the rod engaging members 32a-f toward the rod engaging members 36a-f may be gradually continued until the rod member 90 is bent about the engaging members 36a-f to provide the rod 90 with a select contour that corresponds to the contour of the template rod 80. For example, as illustrated in FIG. 9, the rod engaging members 32a-f have been moved toward the rod engaging members 36a-f such that the rod member 90 is compressed between the rod engaging faces 33a-f, 37a-f to thereby form multiple bends in the rod member 90 which correspond to the bends in the template rod 80. Although FIG. 9 illustrates the rod 90 as being provided with a particular contour or curvature, it should be appreciated that the desired configuration of the rod 90 may include one or more bends that are more or less pronounced than those illustrated in FIG. 9, it being understood that the shape/contour of the template rod 80 may be modified or changed to correspond to different arrangements and positions of the bone anchors attached to the spinal column to which the rod 90 will ultimately be engaged.

As indicated above, the heating element 60, 160 or the environmental chamber 160' heats the rod 90 to a temperature which tends to reduce rigidity and increase flexibility of the rod 90 to facilitate bending. It should be appreciated that the heating element 60, 160 or the environmental chamber 160' may apply heat to the rod 90 prior to bending of the rod 90 and/or concurrently with bending of the rod 90. Once the rod 90 is bent to a desired configuration, the heating element 60, 160 or the environmental chamber 160' is deactivated (or heating is reduced) to allow the rod 90 to cool to a temperature below the glass transition temperature $T_g$. As the rod 90 returns to a temperature below $T_g$, the rod material becomes more rigid and freezes the rod 90 in the desired shape/configuration to maintain the curvature or contour formed in the rod 90. A fan and/or a cooling element (discussed below) may also be used to decrease the temperature of the rod 90 in a controlled and expedited manner to facilitate prompt removal of the rod 90 from the bending mechanism 11. Once the rod 90 has cooled and has become sufficiently rigid, the rod engaging members 32a-f and 36a-f may be moved away from one another, as indicated by arrows B and D, respectively, and the rod 90 may be removed from the bending mechanism 11. The rod 90 may then be engaged with the bone anchors attached to the spinal column and checked for proper fit. If the contour or curvature of the rod 90 must be adjusted to provide a more accurate fit, the rod 90 may be reinserted into the bending mechanism 11 of the device 10 to provide additional bending or contouring of the rod 90.

Other operations are also contemplated for bending the rod 90 in addition to those specifically described above with respect to FIGS. 6-9. For example, in one form, the template rod 80 may be maintained within the rod receiving area 40, and the rod 90 may be compressed against the template rod 80 during the bending process. In another form, after each of the rod engaging members 32a-f, 36a-f has been moved into engagement with the template rod 80, the particular positions of each of the engaging members 32a-f, 36a-f relative to the rod receiving area 40 is marked and/or recorded, either mechanically or electronically. The rod engaging members 32a-f, 36a-f may then be moved away from one another and the rod receiving area 40, and the template rod 80 may be removed from the rod receiving area 40 and replaced by the rod 90. The heating element 60 can then be actuated to heat the rod 90 as described above, and each of the rod engaging members 32a-f, 36a-f can be moved back to their marked and/or recorded position to bend the rod 90 to a shape/contour that corresponds to the shape/contour of the template rod 80.

Figure 10:
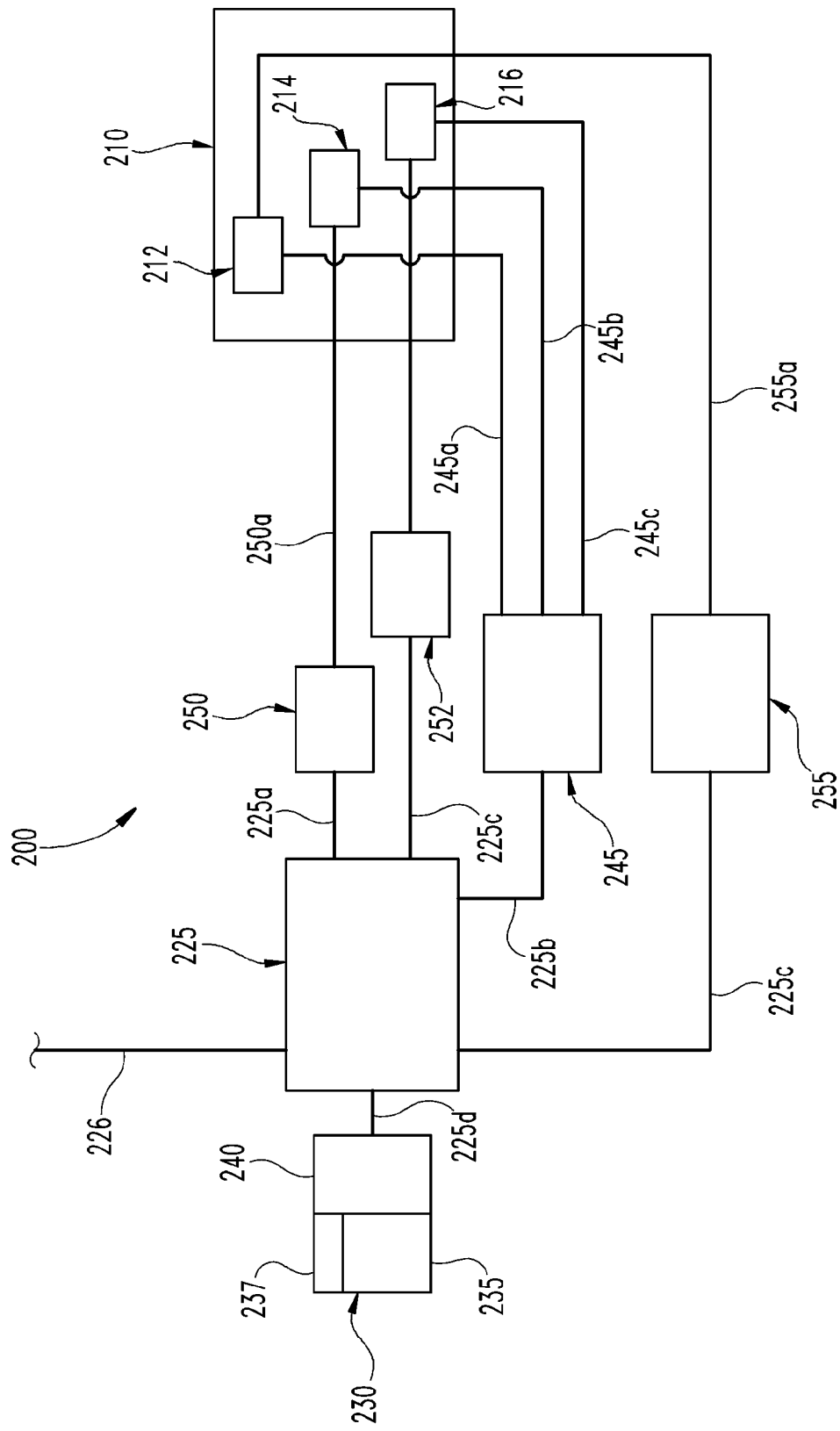
FIG. 10 is a schematic diagram illustrating a system according to one form of the invention for bending/contouring an elongate member.

Referring now to FIG. 10, shown therein is a schematic illustration of a system 200 for bending the rod 90 to a desired curvature or contour. The system 200 includes a rod bending device 210 that generally includes a bending mechanism 212 and a heating element 214. The rod bending device 210 may optionally be provided with a cooling element 216. It should be appreciated that the bending mechanism 212 may be configured similar to the bending mechanism 11 illustrated and described above with regard to the device 10. Additionally, it should be understood that various features and characteristics described above with respect to the heating element 60, 160 and the environmental chamber 160' are equally applicable to the heating element 214 and/or the cooling element 216. It should also be understood that one or more features associated with the heating element 214 and the cooling element 216 may be incorporated into an integrated heating/cooling element.

Besides the rod bending device 210, the system 200 may also be provided with a controller 225, a user interface 230, a sensing arrangement 245, a heat source 250, and an optional cooling source 252. The system 200 may also include one or more actuating members 255 for regulating or controlling actuation of the bending mechanism 212.

The sensing arrangement 245 includes one or more sensors structured to monitor one or more operating functions associated with the device 210. For example, the operating functions monitored by the sensing arrangement 245 may include sensing/monitoring of the heating function provided by the heating element 214 and/or sensing/monitoring of the cooling function provided by the cooling element 216 via one or more temperature sensors or thermocouples. Additionally, the operating functions monitored by the sensing arrangement 245 may also include sensing/monitoring of the pressure applied to the rod 90 by the bending mechanism 212 and/or the actuating members 255 via one or more feedback or pressure sensors, and/or sensing/monitoring of the relative position/orientation of the rod engaging members associated with the first and second engaging portions via one or more position sensors.

In the illustrated embodiment, the sensing arrangement 245 is electronically coupled to the bending mechanism 212 via pathway 245a and includes one or more feedback or pressure sensors configured for sensing/monitoring the amount of pressure applied to the rod 90 by the bending mechanism 212. The sensing arrangement 245 is electronically coupled with the heating element 214 via pathway 245b, and includes one or more temperature sensors or thermocouples configured for sensing/monitoring the heating function provided by the heating element 214, and/or to directly sense/monitor the temperature of one or more portions of the rod 90. The sensing arrangement 245 is electronically coupled with the cooling element 216 via pathway 245c, and includes one or more temperature sensors or thermocouples configured for sensing/monitoring the cooling function provided by the cooling element 216, and/or to directly sense/monitor the temperature of one or more portions of the rod 90. The sensing arrangement 245 may also be electronically coupled to the bending mechanism 212 via a pathway connected to one or more position sensors configured for sensing/monitoring the relative position of the rod engaging members. In one embodiment, the sensing arrangement 245 may be structured to sense/monitor the temperature of the heating element 214 and the cooling element 216. In another embodiment, the sensing arrangement 245 may be structured to directly sense/monitor the temperature of one or more portions of the rod 90. In a further embodiment, the sensing arrangement 245 may be structured to sense/monitor the temperature of the bending mechanism 212. The sensing arrangement 245 is further structured to provide an electronic sensor signal corresponding to the sensed pressure, temperature and/or position to the controller 225 along pathway 225b to the controller 225.

In one embodiment, the controller 225 operates in accordance with operating logic to receive and process the sensor signals to determine if a change in temperature, pressure and/or position is required. It may be desirable to maintain a particular balance of the temperature and pressure to avoid undesired deformation or fracturing/breaking of the rod 90. For example, excessive heat could possibly cause the rod 90 to melt and/or degrade or negatively affect the material properties of the rod 90, while excessive pressure could cause rod the 90 to improperly deform, break and/or degrade or negatively affect the material properties of the rod 90. In one embodiment, the controller 225 is comprised of one or more components that may be configured as a single unit, or may alternatively be distributed among two or more units. Such components may be of a solid state, electromagnetic, optical, and/or other configurations that would occur to those skilled in the art. The controller 225 may include analog circuitry, digital circuitry, and/or a hybrid combination of both. In one embodiment, the controller 225 is of the programmable variety that executes algorithms and processes data in accordance with operating logic defined by programming instructions (i.e., software or firmware). Alternatively or additionally, the operating logic for the controller 225 may be at least partially defined by hardwired logic or other hardware.

As further illustrated in FIG. 10, the controller 225 includes a power supply 226 which may supply power to the controller 225 from an external source, such as an electrical socket. In another non-illustrated embodiment, a power supply may be located internally within the controller 225 and may be provided, for example, in the form of one or more electrochemical cells or a battery of cells. It should be appreciated that the controller 225 may be modified for use with a DC power source or an AC power source, and that the modification of components may be dependent upon the availability of one or more forms of the power source. Additional variations to the controller 225 will become apparent with respect to various configurations of the system 200. It should also be appreciated that the controller 225 may provide power to the other components of the system 200 such as the user interface 230, the heat source 250, the cooling source 252, the bending mechanism 212, the actuating member 255 and/or the sensing arrangement 245. Alternatively, power may be provided to one or more of these components directly via a dedicated power source.

After the controller 225 receives and processes one or more of the sensor signals, one or more controller output signals are sent to the user interface 230 via pathway 225d. In one example, the controller output signals may include a temperature output signal, a pressure output signal and/or a position output signal corresponding to the relative positioning of the engaging members. The user interface 230 may include a visual display 235 and/or an audio component 237 configured to provide one or more indications corresponding to the output signal to a user, and which may identify any necessary changes, if any, to the temperature, pressure and/or position. The visual display 235 can be of a Cathode Ray Tube (CRT) type, Liquid Crystal Display (LCD) type, plasma type, Organic Light Emitting Diode (OLED) type, a printer, or other types of output devices as would occur to those skilled in the art. The user interface 230 may also include a user input 240 wherein a user may enter commands, data, or programming instructions. Additionally or alternatively, a user may enter other information at the user input 240 relevant to the bending process, such as the type of material from which the rod 90 is formed and/or a desired amount of heat to be applied by the heating element 214, just to name a few possibilities. The user input 240 may include a keyboard, mouse or other pointing device, a voice recognition input subsystem, and/or different operator input apparatus as would occur to those skilled in the art.

As one example of a response to the indication provided by the visual display 235 and/or the audio component 237, the user may provide an input signal at the user input 240 which indicates that the temperature of the heat provided by the heating element 214 needs to be increased, decreased or maintained. The input signal may be transmitted to the controller 225 along the pathway 225d, received and processed by the controller 225, and a corresponding output signal may be provided by the controller 225 to the heat source 250 and/or the cooling source 252 via pathways 225a, 225c. The heat source 250 and/or the cooling source 252 then control the heating element 214 and/or the cooling element 216, which in turn controls/regulates the temperature of the rod 90. While the heat source 250 and the heating element 214 have been illustrated as separate components, it should be appreciated that in alternative embodiments, the heat source 250 and the heating element 214 may be provided as a single, integrated component. Additionally, while the cooling source 252 and the cooling element 216 have been illustrated as separate components, it should be appreciated that in alternative embodiments, the cooling source 252 and the cooling element 216 may be provided as a single, integrated component. Furthermore, it should be appreciated that in alternative embodiments, the heating element 214 and the cooling element 216 may also be provided as a single, integrated component. Moreover, as alternatives to the foregoing, the controller 225 may automatically control/regulate the heating element 214 and the cooling element 216 in response to the sensor signal without any user input, or a user could directly input a temperature change at the heat source 250 or the cooling source 252 in response to the indication provided by the visual display 235 and/or the audio component 237.

As an additional or alternative response to the output signal provided by the display 235, the user may increase, decrease or maintain the amount of pressure applied to the rod 90 by the bending mechanism 212. For example, when the rod bending device 210 is configured similar to the rod bending device 10, a user may manually adjust the position of the engaging members (not shown in FIG. 10) relative to the rod receiving area 40 to correspondingly adjust the amount of pressure applied to the rod 90. Alternatively, the system 200 may include an actuating member 255 structured to provide and control/regulate actuation of the bending mechanism 212 and/or the relative positions of the rod engaging members. In one form, the actuating member 255 may include an electronic or pneumatic motor configured to control positioning of the rod engaging members relative to one another and relative to the receiving area. In another form, the actuating member 255 may be provided as a hydraulic arrangement including a hydraulic device configured to provide and regulate actuation of the bending mechanism 212. In one particular aspect of this form, the device may be configured to provide back pressure or an electronic feedback signal in response to an amount of force applied by a user to the bending mechanism 212 to limit the amount of force applied by, and/or the rate of actuation of, the bending mechanism 212. In still other embodiments, the actuating member 255 may be provided with other types of mechanical arrangements configured to provide and regulate actuation of the bending mechanism 212.

When the system 200 includes actuating member 255, the user can provide an input signal at the user input 240 which indicates the desired amount of pressure to be applied to the rod 90 by the bending mechanism 212. Alternatively, the user can provide an input signal at the user input 240 which indicates the desired relative positioning of the rod engaging members. The input signal may be transmitted to the controller 225 along the pathway 225d, received and processed by the controller 225, and a corresponding output signal may be provided by the controller 225 to the actuating member 255 via pathway 225c. The actuating member 255 then communicates with the bending mechanism 212 via pathway 255a in correspondence to the output signal to regulate the amount of pressure applied on the rod 90 by the bending mechanism 212 or otherwise control the relative positioning of the rod engaging members of the bending mechanism 212. While the actuating member 255 and the bending mechanism 212 have been illustrated as separate components, it should be appreciated that in alternative embodiments, these separate components could be combined into a single, integrated component. Furthermore, as alternatives to the foregoing, the controller 225 may automatically regulate the pressure applied to the rod 90 by the bending mechanism 212 in response to a sensor signal without any user input, or a user could directly input a pressure change at the actuating member 255 in response to the indication provided by the display 235 or the audio component 237.

As indicated above, the controller 225 may be programmed to operate in accordance with operating logic to automatically or semi-automatically control various functional and operational aspects of the system 200. In other words, the controller 225, in cooperation with the user interface 230 and the sensing arrangement 245, may be programmed to automatically monitor and control various functional and operational aspects of the rod bending device 210 including the bending mechanism 212, the heating element 214 and/or the cooling element 216. In one embodiment, the controller 225 is programmable to contour or bend the rod 90 to define two-dimension or three-dimensional curvatures, including a single curved portion or multiple curved portions. Additionally, the controller 225 may be programmed to provide the rod 90 with one or more linear portions so as to provide the rod 90 with a curvilinear configuration. In another embodiment, the controller 225 is programmable to contour or bend the rod 90 using a predefined heating, bending and/or cooling profile that automatically controls heating of the rod 90 via the heating element 214, bending of the rod via the bending mechanism 212, and/or cooling of the rod 90 via the cooling element 216. In a further embodiment, the controller 225 is programmable to bend a rod 90 that is formed of a particular material or combination of materials (i.e., PEEK, a PEEK composite material, titanium, a titanium alloy, CoCr, Nitinol, etc.), that is provided with a particular outer cross-sectional shape (i.e., circular, elliptical, square, rectangular, polygonal, etc.), and/or that is provided with a particular outer cross-sectional size, and/or a particular rod configuration (i.e., solid, hollow, inner core within an outer sleeve, etc.). In each of these embodiments, the controller 225 may be programmed via the user interface 230 and/or may be programmed via loading a program or operating logic from internal memory of the controller 225, from a memory media or from a remote memory location.

Furthermore, the controller 225, in cooperation with the sensing arrangement 245, may be programmed to limit or regulate various functional and operational aspects of the rod bending device 210 to prevent damage or weakening of the rod 90 and/or one or more elements or components of the system 200. For example, the controller 225 may be programmed to limit or regulate the bending pressure exerted onto the rod 90 via the rod bending device 210, to limit or regulate the amount of heat applied to the rod 90 via the heating element 214, and/or to limit or regulate the rate of heating or cooling of the rod 90 via the heating element 214 and/or the cooling element 216. As should be appreciated, programming the controller 225 to limit or regulate various functional and operational aspects of the rod bending device 210 may prevent breakage or comprising the mechanical strength of the rod 90 and/or one or more elements or components of the system 200.

In a further embodiment, the system 200 is configured to provide real-time, dynamic control of the rod bending process. It may be particularly desirable to maintain a balance of the temperature and pressure to avoid undesired deformation or fracturing/breaking of the rod 90. For example, the system 200 may be configured to automatically control the amount of heat and/or pressure applied to the rod 90 during the bending process to avoid undesired deformation of the rod 90 or a negative effect on the material properties of the rod 90. As should be appreciated, excessive heat or an excessive heating rate could possibly cause the rod 90 to melt and/or degrade or negatively affect the material properties of the rod 90, while excessive pressure could cause the rod 90 to improperly deform, break and/or degrade or negatively affect the material properties associated with the rod 90. In one particular form of control, the system 200 is configured to gradually increase the bend/curve in the rod 90 until a desired curvature or contouring of the rod 90 is achieved. Once the desired configuration is achieved, the system 200 is operable to selectively eliminate or reduce the heat and/or pressure applied to the rod 90. Particularly, the system 200 may eliminate or reduce the application of heat to the rod 90 via regulation of the heating elements 214 and/or the cooling element 216 to in turn adjust the temperature of the rod 90 to a target temperature, and deactuation of the bending mechanism 212 and removal or reduction of the pressure applied to the rod 90. The rod 90 can then be removed from the bending mechanism 212 and checked for proper fit in an orthopedic construct. Alternatively, the rod 90 may be repositioned in the bending mechanism 212, and one or more additional bends may be formed in the rod 90.

Still other modifications and variations to the system are contemplated. As indicated above, the system 200 may be provided with a sensing arrangement 245 including sensors structured to monitor one or more functional or operational aspects associated with the device 210, including the sensing/monitoring of the heating function provided by the heating element 214 and/or sensing/monitoring of the cooling function provided by the cooling element 216 via one or more temperature sensors or thermocouples. After the rod 90 has been loaded into/onto the device 210, the rod 90 is heated to a predetermined temperature, and is preferably heated at a predetermined heating rate. Once the rod 90 has been heated to a predetermined temperature or temperature range, the user interface 230 may generate a perceptible signal (i.e., a visual signal or an audible signal) that indicates that the rod 90 is ready for bending. The bending mechanism 212 may then by actuated, either automatically or manually, to bend the rod to a particular contour. The temperature of the rod 90 may be monitored during the bending process and the temperature of the rod 90 adjusted via actuation of the heating element 214 and/or the cooling element 216 to maintain the rod 90 within an acceptable temperature range. After the rod 90 is bent, the temperature of the rod 90 may be reduced via actuation of the cooling element 216, and is preferably cooled at a predetermined cooling rate. Controlled cooling of the rod 90 provides increased stability and allows for prompt removal of the rod 90 from the bending device 210.

In another embodiment, a device for bending an elongate member is provided, including a bending mechanism having a plurality of engaging members. Each of the plurality of engaging members is selectively positionable relative to a portion of the bending mechanism structured for receiving the elongate member. The device also includes a heating element arranged to apply heat to the elongate member when the elongate member is positioned at the bending mechanism.

In still another embodiment, a system is provided which includes a bending device with a first rod engaging portion positioned generally opposite a second rod engaging portion. The device also includes a heating element arranged to apply heat to an area adjacent the first and second rod engaging portions. The system also includes a template rod that has a contoured profile and a spinal rod formed of a heat deformable material. At least one of the first and second rod engaging portions includes an arrangement having a shape/contour corresponding generally to the shape/contour of the template rod. The spinal rod is positioned in a space between the first and second rod engaging portions and the heating element is arranged to apply heat to the spinal rod to increase flexibility of the spinal rod to facilitate bending of the spinal rod relative to the arrangement upon actuation of the bending device.

In yet another embodiment, a method is provided for bending an elongate member of an orthopedic construct includes: providing an elongate member; providing a device including a bending mechanism structured to receive the elongate member at a space between a first rod engaging portion and a second rod engaging portion, and a heating element arranged to apply heat to the elongate member; arranging at least one of the first and second rod engaging portions to correspond in shape to a desired shape of the elongate member; positioning the elongate member within the bending mechanism; heating the elongate member with the heating element; and bending the elongate member to the desired shape by actuating the bending mechanism.

Any theory, mechanism of operation, proof, or finding stated herein is meant to further enhance understanding of the present invention, and is not intended to make the present invention in any way dependent upon such theory, mechanism of operation, proof or finding. It should be understood that while the use of the word preferable, preferably or preferred in the description above indicates that the feature so described may be more desirable, it nonetheless may not be necessary, and embodiments lacking the same may be contemplated as within the scope of the application, that scope being defined by the claims that follow. In reading the claims, it is intended that when words such as "a", "an", "at least one", and "at least a portion" are used, there is no intention to limit the claim to only one item unless specifically stated to the contrary in the claim. Further, when the language "at least a portion" and/or "a portion" is used, the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected.

What is claimed is:

1. A device for bending an elongate member used in a medical procedure, comprising:
    a bending mechanism including
    a housing having a top wall, a bottom wall, a first lateral side wall and a second lateral side wall, a front wall and a back wall, wherein a surface of the top wall defines a first set of a plurality of elongated apertures and a second set of a plurality of elongated apertures;
    a receiving area and a plurality of engaging members, said receiving area extending generally along a longitudinal axis and sized to receive the elongate member, a first set of said engaging members positioned on a first side of said receiving area and being configured to move laterally and rotationally within the first set of elongated apertures for selective positioning of the first set of elongated members at select locations along the first set of elongated apertures and a second set of said engaging members positioned on a second side of said receiving area opposite said first side, the second set of engaging members being configured to move laterally and rotationally within the second set of elongated apertures for selective positioning of the second set of elongated members at select locations along the second set of elongated apertures and wherein at least some of said engaging members are movable in a lateral direction to position said movable engaging members at select locations to compressingly engage the elongate member between said first and second sets of engaging members to form one or more bends in the elongate member; and
    a heating element configured to apply heat to one or more portions of the elongate member when the elongate member is positioned in said receiving area to facilitate bending of the elongate member by said bending mechanism.

2. The device of claim 1, wherein said lateral direction of movement of said movable engaging members comprises substantially linear movement that is generally perpendicular to said longitudinal axis.

3. The device of claim 1, wherein said movable engaging members include an engaging face that is positioned in contact with said elongate member, said engaging face defining a recess sized and configured to receive a portion of said elongate member therein.

4. The device of claim 3, wherein said recess has a C-shaped configuration.

5. The device of claim 3, wherein said recess has a V-shaped configuration.

6. The device of claim 3, wherein said recess has an enclosed configuration to fully enclose said portion of said elongate member.

7. The device of claim 1, wherein said engaging members of said first set are axially offset from said engaging members of said second set in a direction along said longitudinal axis.

8. The device of claim 1, wherein at least some of said engaging members are rotatable about an axis of rotation arranged generally perpendicular to said lateral direction of movement of said movable engaging members.

9. The device of claim 1, wherein said heating element is structured and arranged to apply heat to select portions of the elongate member to facilitate bending of said select portions by said bending mechanism to form said one or more bends.

10. The device of claim 1, wherein said heating element is generally positioned above said receiving area of said bending mechanism.

11. The device of claim 1, wherein said housing defining an internal chamber, said heating element positioned within said internal chamber and generally positioned beneath said receiving area of said bending mechanism.

12. The device of claim 1, wherein said heating element comprises an environmental chamber including an interior region within which said bending mechanism and said elongate member are positioned.

13. The device of claim 1, further comprising means for moving said movable engaging members in said lateral direction.

14. The device of claim 1, further comprising an elongate template member that is deformable to a contoured configuration extending along a contour axis, said contoured configuration of said template member positionable in said receiving area of said bending mechanism with said first and second sets of engaging members arranged relative to said template member to establish a pathway between said first and second sets of engaging members extending generally along said contour axis, said contour axis generally corresponding to a desired contour of the elongate member including said one or more bends.

15. A system for bending an elongate rod used in a medical procedure, comprising:
a bending device, including: a housing having a top wall, a bottom wall, a first lateral side wall and a second lateral side wall, a front wall and a back wall, wherein a surface of the top wall defines a first set of a plurality of elongated apertures and a second set of a plurality of elongated apertures; a rod receiving area extending generally along a longitudinal axis; a first rod engaging portion including a first set of rod engaging members positioned on a first side of said rod receiving area and the first set of rod engaging members being configured to move laterally and rotationally within the first set of elongated apertures for selective positioning of the first set of rod engaging members at select locations along the first set of elongated apertures; a second rod engaging portion including a second set of rod engaging members positioned on a second side of said rod receiving area opposite said first side and the second set of rod engaging members being configured to move laterally and rotationally within the second set of elongated apertures for selective positioning of the second set of elongated members at select locations along the second set of elongated apertures; A connector configured to connect said rod engaging member to said top wall of said housing; an elongate spinal rod formed of a heat deformable material, said elongate spinal rod positioned within said rod receiving area of said bending device; and a heating element arranged to apply heat to one or more portions of said elongate spinal rod to increase flexibility of said one or more portions to facilitate bending of said elongate spinal rod; and wherein at least some of said rod engaging members are movable in a lateral direction to position said movable rod engaging members at select locations to compressingly engage said elongate spinal rod between said first and second sets of rod engaging members to form one or more bends in said elongate spinal rod, and wherein threading of said connector fixes the rod engaging member to the housing and unthreading of said connector unclamps the rod engaging members from the housing allowing for adjustment of the position and orientation of the rod engaging members.

16. The system of claim 15, wherein said rod engaging members include an engaging face that is positioned in contact with said elongate spinal rod, said engaging face defining a recess sized and configured to receive a portion of said elongate spinal rod therein.

17. The system of claim 15, wherein said rod engaging members of said first set are axially offset from said rod engaging members of said second set in a direction along said longitudinal axis.

18. The system of claim 15, wherein said heating element is structured and arranged to apply heat to select portions of said elongate spinal rod to facilitate bending of said select portions by said bending device to form said one or more bends.

19. The system of claim 15, wherein said heating element comprises an environmental chamber including an interior region within which said bending device and said elongate spinal rod are positioned.

20. The system of claim 15, further comprising at least one sensor structured and arranged to monitor one or more operating functions of said bending device and said heating element to provide a corresponding sensor output signal.

21. The system of claim 20, wherein said one or more operating functions include at least one of a pressure applied to said elongate spinal rod by said bending device and a temperature of said heat applied to said elongate spinal rod by said heating element.

22. The system of claim 20, wherein said at least one sensor includes at least one temperature sensor arranged to sense a temperature of said elongate spinal rod upon application of said heat.

23. The system of claim 15, wherein said heat deformable material comprises a polymer-based material.

24. The system of claim 15, wherein said heat deformable material comprises a thermoplastic material.

25. The system of claim 15, wherein said heat deformable material comprises a PEEK material.

26. The system of claim 15, wherein said elongate spinal rod is formed of a composite material comprising a thermoplastic material and a reinforcement material.

27. The system of claim 26, wherein said reinforcement material comprises a carbon material.

28. The system of claim 15, wherein said elongate spinal rod is formed as a composite structure comprising an inner core formed of a first material and an outer sleeve extending about said inner core and formed of a second material different from said first material.

29. The system of claim 28, wherein said first material comprises a metallic material and said second material comprises a thermoplastic material.

* * * * *